US00PP29475P2

(12) United States Plant Patent
Burns

(10) Patent No.: US PP29,475 P2
(45) Date of Patent: Jul. 10, 2018

(54) ***CEPHALANTHUS* PLANT NAMED 'BAILOPTICS'**

(50) Latin Name: *Cephalanthus occidentalis*
Varietal Denomination: Bailoptics

(71) Applicant: Bailey Nurseries, Inc, Newport, MN (US)

(72) Inventor: Jon Burns, Saint Paul, MN (US)

(73) Assignee: BAILEY NURSERIES, INC., New Port, MN (US)

( * ) Notice: Subject to any disclaimer, the term of this patent is extended or adjusted under 35 U.S.C. 154(b) by 0 days.

(21) Appl. No.: 15/330,434

(22) Filed: Sep. 20, 2016

(51) Int. Cl.
*A01H 5/02* (2018.01)

(52) U.S. Cl.
USPC ..... Plt./226

(58) Field of Classification Search
USPC ..... Plt./226
See application file for complete search history.

(56) References Cited

PUBLICATIONS

JCRaulston Arboretum at NC State University. 2017 Information on *Cephalanthus occidentalis* 'Bailoptics'. https://jcra.ncsu.edu/horticulture/our-plants/results-by-name-serial-number.php?serial=129189. 1 page.*

* cited by examiner

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Cephalanthus* plant named, 'Bailoptics', that is characterized by its compact growth habit reaching 1.5 to 1.8 m in height and width, and its new stem growth that is reddish brown in color.

2 Drawing Sheets

Botanical classification: *Cephalanthus occidentalis*.
Variety denomination: 'Bailoptics'.

BACKGROUND OF THE INVENTION

The present invention relates to a new and distinct cultivar of *Cephalanthus occidentalis* and will be referred to hereafter by its cultivar name, 'Bailoptics'. 'Bailoptics' is a new cultivar of buttonbush, a deciduous shrub grown for use as an ornamental landscape plant.

The new cultivar was discovered by the Inventor in summer of 2005 as a seedling that was growing in a seedling block of seed planted from unnamed and unpatented plants of *Cephalanthus occidentalis* in Hastings, Minn.

Asexual propagation of the new cultivar was first accomplished by stem cuttings by the Inventor in June of 2006 in Cottage Grove, Minn. Asexual propagation by stem cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'Bailoptics' as a unique cultivar of *Cephalanthus*.

1. 'Bailoptics' exhibits a compact growth habit reaching 1.5 to 1.8 m in height and width.
2. 'Bailoptics' exhibits new stem growth that is reddish brown in color.

Typical plants of *Cephalanthus occidentalis* differ from 'Bailoptics' in having new stem growth that is green in color and a plant habit that is less compact with a larger plant size (1.8 to 2.5 m in height and 1.8 to 2.4 m in width). 'Bailoptics' can be compared to the *Cephalanthus occidentalis* cultivars 'SMCOSS' (U.S. Plant Pat. No. 26,543) and 'J.N. Select A' (not patented). Both are similar to 'Bailoptics' in having globular-shaped white flowers in mid-summer. 'SMCOSS' differs from 'Bailoptics' in having a more compact plant habit and a smaller plant size, new stem growth that is green in color, a blooming period that is 1 to 2 weeks later, and in producing seeds that are red in color. 'J.N. Select A' differs from 'Bailoptics' in having a larger plant size and foliage that is darker green in color.

BRIEF DESCRIPTION OF THE DRAWINGS

The accompanying colored photographs illustrate the overall appearance and distinct characteristics of the new *Cephalanthus*. The photographs were taken of nine year-old plants of 'Bailoptics' as grown outdoors in a trail garden in Cottage Grove, Minn.

The photograph in FIG. 1 provides a side view of plants of 'Bailoptics' in bloom.

Figure 1:
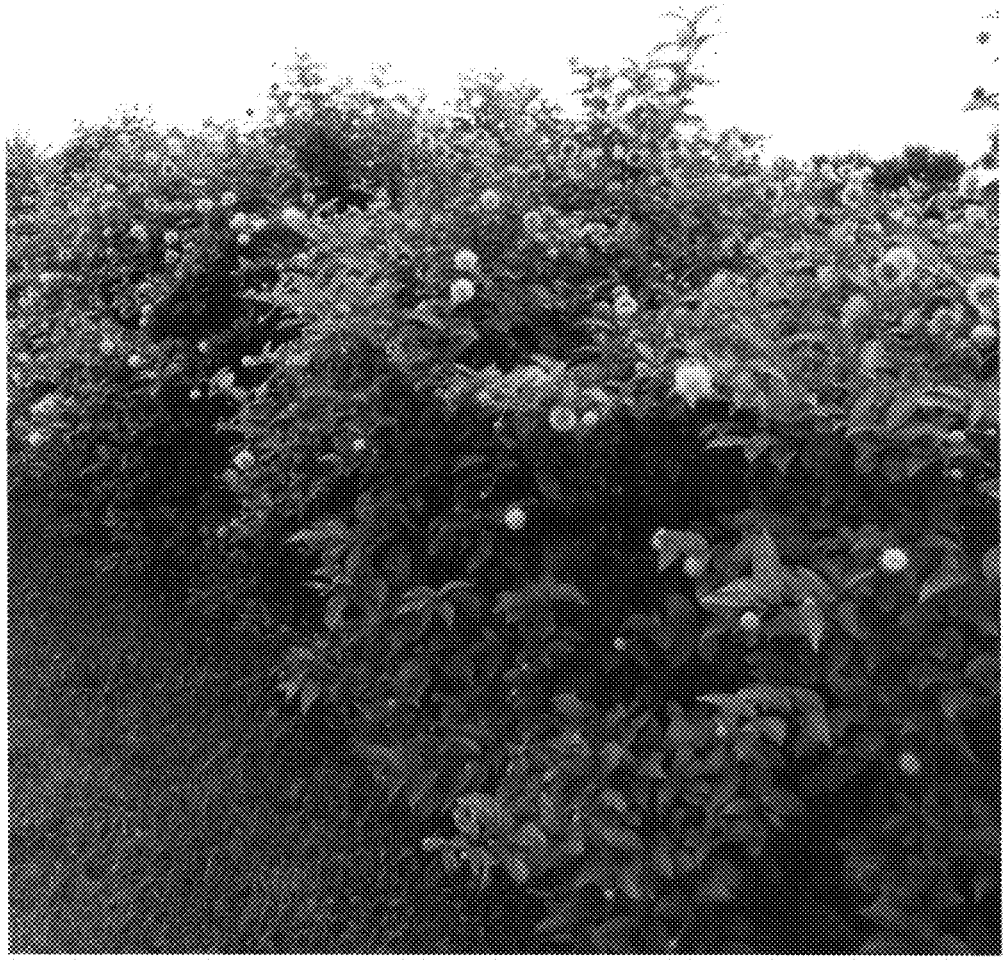
Figure 2:
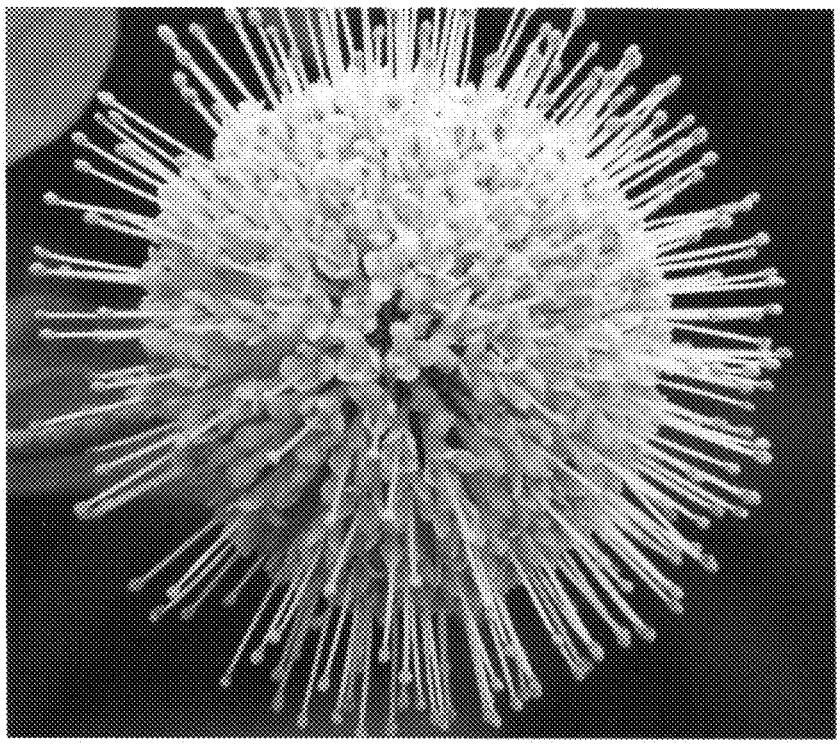

The photograph in FIG. 2 provides a close-up view of an inflorescence of 'Bailoptics'.

Figure 3:
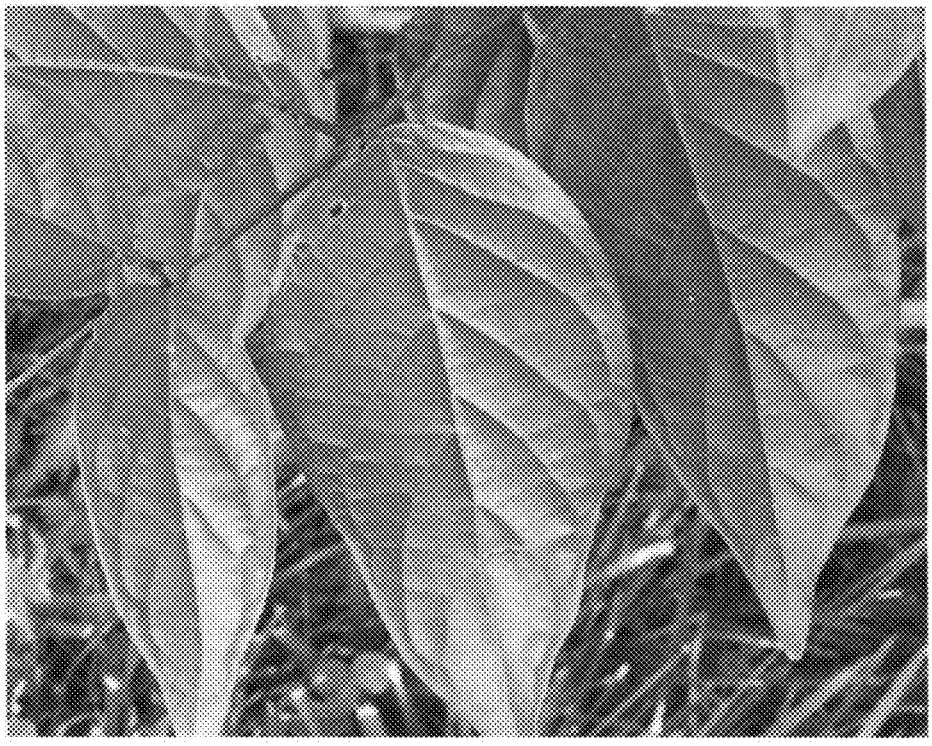

The photograph in FIG. 3 provides a close-up view of the foliage of 'Bailoptics'.

The colors in the photographs are as close as possible with the photographic and printing technology utilized and the color values cited in the Detailed Botanical Description accurately describe the colors of the new *Cephalanthus*.

DETAILED BOTANICAL DESCRIPTION OF THE PLANT

The following is a detailed description of two year-old plants (from a liner) of the new cultivar as grown outdoors in a 2-gallon container in Newport, Minn. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—4 to 5 weeks beginning in late June in St. Paul, Minn.

*Plant type.*—Deciduous perennial shrub.

*Plant habit.*—Compact, upright to spreading outwards.

*Plant height and width.*—An average of 86 cm in height and 75 cm in width as grown in a 2-gallon container, reaches 1.5 to 1.8 m in height and width in 4 years in the landscape.

*Diseases and pests.*—No diseases or pests problems have been observed.

*Hardiness.*—At least in U.S.D.A. Zones 5 to 9.

*Root description.*—Fibrous and fine, 155A in color.

*Propagation.*—Stem cuttings.

*Root development.*—35 days to root cuttings and 3 months to fully develop in a liner at 20° C.

*Growth rate.*—Moderate.

Stem description:

*Shape.*—Rounded.

*Stem color.*—Young stems; 145A, flushed with a blend of 152A and N167A, mature wood; a blend of 183A, 199A and 198A.

*Stem quantity.*—An average of 5 main stems and 8 lateral stems per main stem.

*Stem size.*—Trunk; an average of 13 cm in length and 6 cm in width, mature main stems; an average of 45 cm in length and 1 cm in width, young stems; an average of 54 cm in length and 4 mm in diameter.

*Stem surface.*—New growth; Glabrous and slightly glaucous, mature wood; dull and smooth, becoming bark-like as it ages.

*Stem strength.*—Strong and flexible.

*Branching.*—Well-branched with new growth emerging in opposite arrangement from axillary nodes.

*Lenticels.*—An average of 6 per 1 $cm^2$ area, oblong to oval in shape, raised surface, woody texture, color; ranges from matching surface color to a mix between 155A and 200A.

Foliage description:

*Leaf shape.*—Elliptic.

*Leaf division.*—Simple.

*Leaf base.*—Rounded.

*Leaf apex.*—Acuminate to acute.

*Leaf fragrance.*—None.

*Leaf venation.*—Pinnate, color; upper surface N144A and lower surface 144D.

*Leaf margins.*—Entire and very slightly pubescent.

*Leaf arrangement.*—Opposite.

*Leaf attachment.*—Petiolate.

*Leaf surface.*—Upper surface; slightly shiny, glabrous, and smooth, lower surface; dull and smooth, main lower vein lightly hirsutulous with hairs NN155D in color.

*Leaf internode length.*—An average of 6.5 cm.

*Leaf size.*—An average of 12 cm in length and 6 cm in width.

*Leaf quantity.*—An average of 10 (5 pairs) per branch 25 cm in length.

*Leaf color.*—Young and mature upper surface; a blend of 137A and 144A, young and mature lower surface; 137A, fall color; same as mature color until leaf drop on both surfaces.

*Petioles.*—An average of 1 cm in length and 2 mm in width, color; young petioles 144A lightly suffused with a blend of 152A and N167A and mature petioles a blend of 152A and N167A, glabrous surface.

*Stipules.*—2, at each node, triangular in shape, held upwards against the stem, truncate base, entire margins, an average of 3 mm in length and 3.5 mm in width, N199C to N199D in color.

Inflorescence description:

*Inflorescence type.*—Terminal cyme with dense spherical inflorescences made up of numerous salverform flowers.

*Inflorescence size.*—An average of 3.5 cm in diameter.

*Inflorescence buds.*—Globose in shape, made up of numerous small outwardly protruding flower buds, N144D in color, an average of 1.6 cm in diameter.

*Flower buds.*—Ovate in shape, rounded apex, truncate base, an average of 1.2 mm in length and 1 mm in width, N144D in color.

*Flower fragrance.*—Light pleasant fragrance.

*Lastingness of inflorescence.*—An average of 5 to 7 days, sepals are persistent.

*Flower quantity.*—An average of 5 inflorescences per branch with an average of 450 flowers per inflorescence.

*Flower type.*—Salverform.

*Flower aspect.*—Outwards from central sphere.

*Flower size.*—An average of 4 mm in diameter and 9 mm in depth.

*Peduncles.*—Up to 5 cm in length and 2 mm in width, a blend of 145C and N167A in color, round in shape, moderately strong, glossy surface is sparsely lenticellate with lenticels that are narrow oblong in shape, an average of 0.5 mm in length, slightly raised and a blend between 145D and N200A in color.

*Pedicels.*—None, sessile to peduncle.

*Calyx.*—Fused to central sphere, subtending the flowers, an average of 1 mm in diameter and 0.5 mm in depth, 145A in color.

*Sepals.*—4, fused to central sphere, apex is unfused and triangular in shape, entire margin, fused base, an average of 0.5 mm in length and width, 145A in color, glabrous surface.

*Petals.*—4, fused into tube with apex of each petal free, tube portion is about 1 cm in length and 1 mm in width, free portion; ovate in shape, about 1 mm in length and width, entire margin, acute apex, glabrous and smooth inner and outer surface, color when opening and when fully open; NN155B.

Reproductive organs:

*Gynoecium.*—1 pistil, about 1.4 cm in length with 0.5 mm in width, extend beyond the petals, style is about 1.3 cm in length, and NN155D in color, stigma is about 0.5 mm in diameter, globose in shape and 144D with irregular marks N199C to N199D in color, inferior ovary is minute in size and NN155D in color.

*Androecium.*—4 stamens, about 2 mm in length, thread-like filaments are adnate to petals NN155D in color, about 2.8 cm in length, basifixed anthers are linear in shape, about 1 mm in length, color; N200B with a blend of 150C and 157A in color, pollen is low in quantity and NN155D in color.

*Seed*.—Numerous achenes (about 60 formed per seed head), Oblanceolate in shape, an average of 1.5 mm in length and 1 mm in width, initially 11C in color and turning N199C to N199D in color when mature.

It is claimed:

1. A new and distinct cultivar of *Cephalanthus* plant named 'Bailoptics' as herein illustrated and described.

* * * * *